United States Patent [19]

Hyvärinen

[11] Patent Number: 5,341,819
[45] Date of Patent: Aug. 30, 1994

[54] METHOD AND DEVICE FOR THE SELECTION OF AN INSOLE AND/OR OF A SHOE THAT ADJUSTS THE POSTURE OF THE FOOT

[75] Inventor: Tuomo Hyvärinen, Orimattila, Finland

[73] Assignee: Karhu-Titan OY, Finland

[21] Appl. No.: 869,337

[22] Filed: Apr. 15, 1992

[30] Foreign Application Priority Data

Apr. 16, 1991 [FI] Finland .................................. 911830

[51] Int. Cl.5 .............................................. A61B 5/103
[52] U.S. Cl. ..................................... 128/779; 33/515
[58] Field of Search ..................... 128/774, 779, 782; 33/512, 515; 73/172; 171/25.12, 58, 238, 239, 244, 245, 261, 264

[56] References Cited

U.S. PATENT DOCUMENTS

| 2,795,953 | 6/1957 | Makowsky | 73/172 |
| 3,726,015 | 4/1973 | Neumann | 33/515 |
| 3,826,145 | 7/1974 | McFarland | 128/782 |
| 3,906,931 | 9/1975 | Terekhov | 128/782 |
| 4,195,643 | 4/1980 | Pratt, Jr. | 128/779 |
| 4,323,080 | 4/1982 | Melhart | 128/774 |
| 4,598,717 | 7/1986 | Pedotti | 128/779 |
| 4,802,494 | 2/1989 | Gardiner | 128/779 |
| 4,876,758 | 10/1989 | Rolloff et al. | 12/142 N |
| 4,917,105 | 4/1990 | Tiitola et al. | 128/779 |

FOREIGN PATENT DOCUMENTS

| 1918521 | 10/1969 | Fed. Rep. of Germany | 128/779 |
| 2619702 | 3/1989 | France | 128/782 |
| 454898 | 6/1975 | U.S.S.R. | 128/779 |

Primary Examiner—Stephen C. Pellegrino
Assistant Examiner—Guy V. Tucker
Attorney, Agent, or Firm—Steinberg, Raskin & Davidson

[57] ABSTRACT

The invention is related to a method for the selection of an insole and/or of a shoe that adjusts the posture of the foot and for determination of the biomechanical mode of operation of the foot. In the method, the determination of the mode of operation of the foot is carried out by placing the foot on a symmetry axis of a measurement base, and the load thus applied by the measurement base to a rigid support base in relation to the symmetry axis of the measurement base is measured. For the measurement, the supposed symmetry axis of the foot to be measured is aligned with the symmetry axis of the measurement base by guiding the position of the foot onto said symmetry axis by the heel and by the toes. The measurement of the load is carried out preferably in two stages so that first the load is measured when the person stands on the measurement bases with straight legs, and thereafter the load is measured when the knees have been bent substantially 45° from the straight posture. The invention also concerns a device intended for carrying out the method.

15 Claims, 2 Drawing Sheets

METHOD AND DEVICE FOR THE SELECTION OF AN INSOLE AND/OR OF A SHOE THAT ADJUSTS THE POSTURE OF THE FOOT

FIELD OF THE INVENTION

The invention concerns a method for the selection of an insole and/or of a shoe that adjusts the posture of the foot and for determination of the biomechanical mode of operation of the foot.

The invention also concerns a device intended for carrying out the method of the selection of an insole and/or of a shoe that adjusts the posture of the foot and for determination of the biomechanical mode of operation of the foot.

BACKGROUND OF THE INVENTION

In a mechanical examination, a human foot is a highly complicated construction. On one hand, the foot must be resilient in order that it could adapt itself to the variations in the environment and in the ground so that, at the same time, it provides the body with adequate support and balance. On the other hand, the foot should be sufficiently rigid to provide an adequate friction in relation to the ground surface, so that the horizontal forces of acceleration and deceleration that arise from the movements of the body can be transferred through the foot.

A number of studies have been performed concerning the foot, and in these studies it has been noticed that only about 40% of the population have so-called "normal" feet, whereas the rest have various faults of posture in their feet.

Faulty postures of feet cause a disturbance in the state of loading of the body and a state of extra strain, which is experienced by the person as disagreeable and which may quite frequently result in pains in the foot, ankle, knee, or in the lumbar region of the back.

Faulty postures of feet are commonly corrected by means of various orthopaedic insoles and orthopaedic shoes, but the choice of suitable orthopaedic insoles and shoes has been problematic in prior art.

In order that it should be possible to choose insoles and shoes of the right type, it must be possible to measure and to determine any faulty postures of the feet as well and reliably as possible. In this respect, with regard to the prior art, reference is made in particular to U.S. Pat. Nos. 4,062,355, 3,358,373, and 2,175,116, all of which concern various devices for the determination of the postures and loads of feet and, based thereon, for the choice of a shoe and/or of an insole of the right type.

The most remarkable drawback of the solutions set forth in the above patents is that their operation is highly complicated and requires high professional skill from the operator. This is why the techniques in accordance with these solutions have not obtained common and everyday use.

Compared with the prior art described in the above patent, a considerable improvement was provided by the method described in the applicant's earlier U.S. Pat. No. 1,278,677 and in the corresponding U.S. Pat. No. 4,917,105, in which method the orthopaedic operation of the foot is determined and, on its basis, a suitable correcting orthopaedic insole and/or shoe is chosen. Said method has been applied in practice, and in these practical applications it has been noticed that, when used correctly, said method provides an excellent and reliable result, whereby a shoe and/or an orthopaedic insole can be chosen for each foot. However, it has been a drawback of the method that the method is time-consuming and requires a relatively good training and quite extensive practical experience from the operator.

Owing to these facts, a need has arisen to develop a rapid and automatic method which is better suitable for auxiliary means in the selling of shoes and insoles in a retail store. Thus, the present invention is expressly intended as an improvement over the method of prior date employed by the applicant.

SUMMARY OF THE INVENTION

In view of achieving the objectives of the invention, in the method of the invention, a determination of the mode of operation of the foot is carried out so that the foot is placed on a measurement base, on the symmetry axis of the measurement base, and the load applied by the measurement base to a rigid support base in relation to the symmetry axis of the measurement base is measured.

The device in accordance with the invention comprises a measurement base supported on a rigid base and provided with measurement detectors for measurement of the loads applied from the measurement base to the rigid base substantially symmetrically in relation to the longitudinal symmetry axis of the measurement base.

By means of the invention, a number of significant advantages are obtained over the prior art, of which advantages, e.g., the following should be stated in this connection.

By means of the method and the device in accordance with the invention, the determination of the posture and of the orthopaedic operation of the feet can be carried out very rapidly, and the operation of the method and of the device does not require long-term and thorough training, so that it is well suitable for use, e.g., in shoe stores.

It is an important advantage of the method and the device of the invention that in the invention the loads applied by the feet to the base are measured irrespective of the reason resulting in the application of loads and in the changes in the loads. In contrast, some prior art methods and devices have been based, e.g., on measurement of the bending-in or bending-out, i.e. the movement of pronation or supination, of the ankle or on measurement of the press pattern of the foot arch. From these measurements, attempts have been made indirectly to judge the application of the loads to the shoe.

Other advantages and characteristic features of the invention come out from the following detailed description of the invention.

BRIEF DESCRIPTION OF THE DRAWINGS

The following drawings are illustrative of embodiments of the invention and are not meant to limit the scope of the invention as encompassed by the claims.

DETAILED DESCRIPTION

It is a basic realization in the method of the invention and in the device that makes use of the method that, when it is known how the foot attempts to load the shoe placed under the foot, on this basis it can be concluded what the construction of the shoe ought to be like in order to give an optimally applied support to the foot. On the other hand, it is known that, in view of the strains on the foot, it is advantageous to attempt to guide the posture and the movement of the foot by means of the shoe in such a way that the lateral movement of the ankle joint is kept within a certain optimal range.

In the method of the invention, the distribution of the load of the foot is studied in relation to the supposed symmetry axis of the foot.

Figure 1:
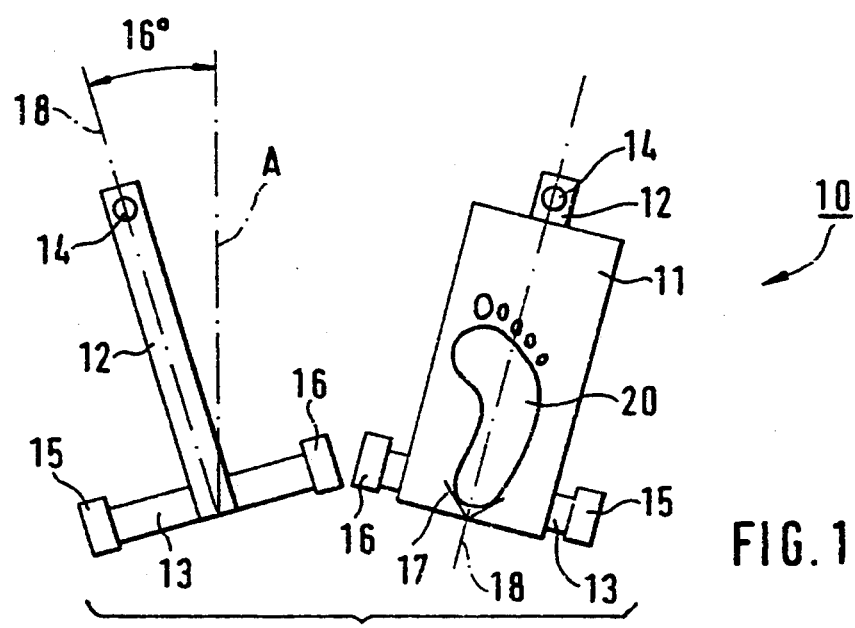
FIG. 1 is a schematic top view of the measurement base of a device in accordance with the invention.

The device in accordance with the invention comprises measurement bases provided for each of the feet, said bases being denoted with the reference numeral 10 in FIG. 1. The measurement base 10 comprises a plate 11, which is supported on a rigid frame by means of a longitudinal frame 12 and a transverse frame 13.

In the exemplifying embodiment shown in FIG. 1, the support is arranged so that on the neutral line 18 of the measurement base, i.e. on the longitudinal symmetry axis of the measurement base, at the front end of the base, an articulated joint 14 is provided which pivots freely in all directions. At its rear part, the measurement base 10 is supported via the transverse frame 13 by means of two support points 15 and 16, which are placed at both sides of the neutral line, i.e. of the symmetry axis. These support points 15 and 16 are provided with force measurement detectors. Further, on the plate 11 of the measurement base, a fork 17 is provided, which guides the foot 20 so that it is placed on the measurement base 10 on the neutral line 18.

According to FIG. 1, the direction of the neutral line, i.e. of the symmetry axis 18 of the measurement base, has been turned preferably 16° outwards from the line A that runs straight forwards, which angle has been noticed to be natural for most people.

Thus, in the method, the foot 20 is placed on the measurement base 10 so that the heel of the foot is guided into the centering guide fork 17 and the root joint of the middle toe in the foot 20 is placed on the neutral line 18 marked on the measurement base 10. In this way the supposed symmetry axis of the foot is aligned with the symmetry axis of the measurement base. Hereupon the distribution of forces is measured by means of the force measurement detectors placed at the support points 15 and 16. Said force measurement detectors are placed symmetrically at both sides of the neutral line. If the load of the foot 20 is distributed symmetrically, the readings of both of the force detectors are equal.

Figure 2:
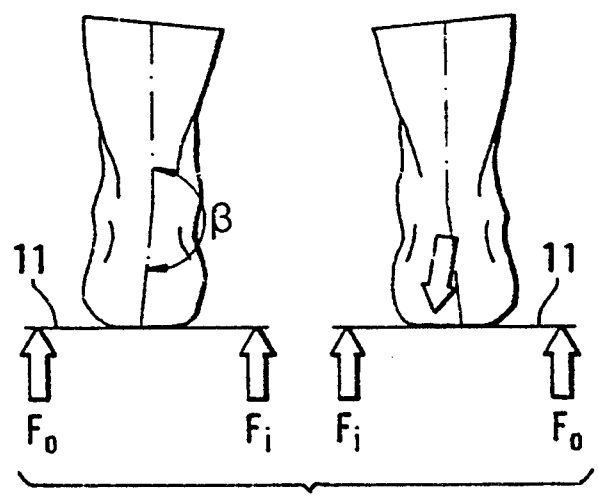
FIG. 2 is a schematic illustration of a situation of measurement, i.e. of a situation in which a person stands on the measurement base of the measurement device.

The load of the inside of the foot, i.e. Fi in FIG. 2, is increased, e.g., by the effect of a low arch of the foot, i.e. a flat foot, and so also by the effect of inward twisting of the ankle joint, i.e. pronation. On the other hand, the load of the outside edge of the foot, i.e. Fo in FIG. 2, is increased, e.g., as a result of a high arch of the foot and as a result of outward twisting of the ankle joint, i.e. supination.

In the method, the ratio of the loads Fi, Fo of the inside and the outside edges of the foot is examined, and from this ratio it is possible to conclude the sort of a shoe that is suitable for giving the correct support to the foot concerned. The ratio of the loads Fi, Fo of the inside and outside edges can be varied by inclining the foot in relation to the shoe by means of a suitable insole and/or shoe that adjusts the posture of the foot, the properties of resilience and hardness of the sole being asymmetric in relation to the central axis of the shoe.

Figure 3:
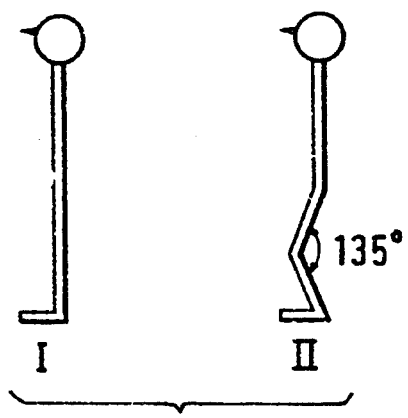
FIG. 3 is a schematic illustration of different stages of measurement.

In the method of the invention, in the second stage of the measurement, which corresponds to the case II in FIG. 3, while standing on the measurement base, the knees are bent forwards from the straight posture substantially 45°, and it is examined how the ratio of the loads Fi, Fo of the inside and outside edges of the foot is changed as compared with the straight standing posture. If the ankle joint has a tendency of increasing its inward or outward twisting while a step is being taken, that comes out during bending of the knees as a shifting of the load further to the outside or inside edge of the foot.

In this so-called knee-bend posture, it is important that the distance between the knees remains substantially invariable, i.e. the same as when standing upright, in order that possible lateral movements of the knees should not cause shifting of the loads to the inside or outside edge. The distance between the knees must be substantially the same as the distance between the heels.

In the invention, it has been noticed that the most appropriate distance is such that the distance between the heels is about 240 mm. This additional information obtained in the knee-bend posture is used in the choice of the shoe or insole to affirm the conclusions that were made on the basis of the distribution of forces measured in the straight standing posture.

In a particular embodiment of the method, the shoes are divided into three groups, i.e. those with neutral conduct, those that resist inward twisting of the ankle, and those that resist outward twisting of the ankle. In a corresponding way, the insoles which support the posture of the foot are divided into neutral insoles, insoles that incline the foot outwards, and insoles that incline the foot inwards. Moreover, there may be several degrees of inclination. On the basis of measurements carried out, those ratios of loads of inside and outside edges have been determined on whose basis the choice of the shoe and/or of the insole is determined.

Above, with reference to FIG. 1, it was ascertained that the measurement base 10 is supported from three points so that the first, i.e. the foremost support point 14 is an articulated joint that pivots in all directions and that the rearmost support points comprise force measurement detectors by whose means the ratio of the loads of the inside and the outside edges of the foot is determined. The device may also be accomplished in a way differing from FIG. 1.

Figure 4:
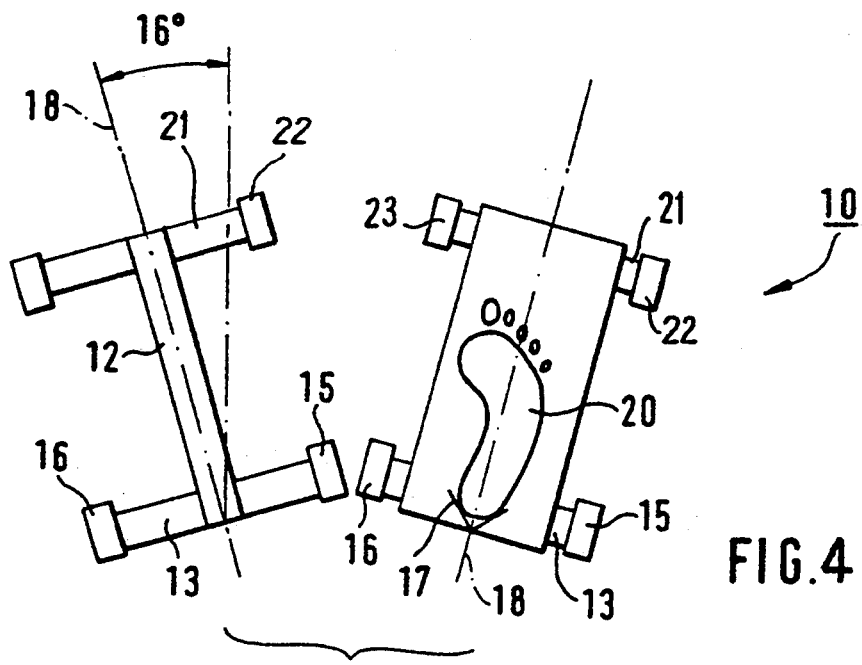
FIG. 4 is a schematic top view of the measurement base of a device in accordance with the invention in which the measurement base is supported at four support points.

As illustrated in FIG. 4, one alternative mode is that the measurement base 10 is supported at four points 15, 16, 22, 23, so that in the front part of the base there are support points 22, 23 at both sides of the neutral line 18 and, correspondingly, in the rear part of the measurement base 10 there are support points 15, 16, for example, in the way illustrated in FIG. 1. The measurement base will thus be supported at its front part via a transverse frame 21 by means of two support points 22, 23 in a manner similar to the support structure of transverse frame 13 and support points 15 and 16 on the rear part of the measurement base 10. However, in such a solution, each of the four support points would have to be provided with a measurement detector of its own, in which case the solution would be substantially more expensive than the three-point suspension shown in FIG. 1. With the use of four points, the accuracy of measurement would, however, not be so much better than with three points that said four-point suspension provided a corresponding advantage. In other respects, the embodiment of FIG. 4 is similar in operation and use to that illustrated in FIG. 1.

Figure 5:
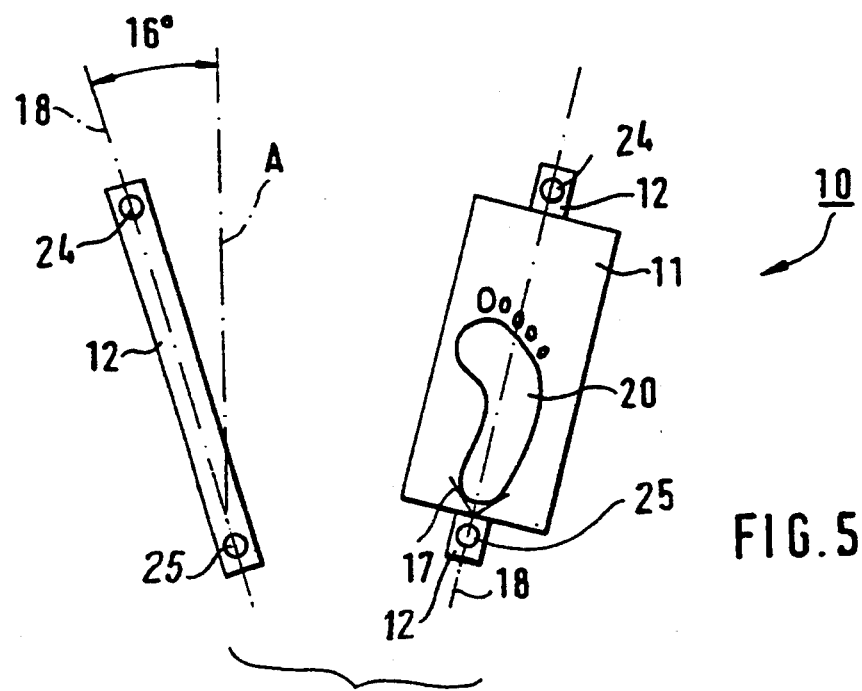
FIG. 5 is a schematic top view of the measurement base of a device in accordance with the invention wherein the measurement base is supported at two support points arranged along a longitudinal symmetric axis of the measurement base.

As illustrated in FIG. 5, one possible alternative device is one in which the measurement base 10 is supported on the rigid frame of the device at two points 24, 25 which are placed on the neutral line 18 of the measurement base 10 and at least one of which is provided with a torque measurement detector. Yet, the very three-point suspension shown in FIG. 1 should be considered the most usable solution. In other respects, the embodiment of FIG. 5 is similar in operation and use to that illustrated in FIG. 1.

Further, it is characteristic of the device that the construction of the force detectors is such that the deformation taking place in them is sufficiently little so that the change in the position of the measurement base 10 does not cause an error in the measurement result. A suitably little and permitted deformation in the measurement detectors can be considered to be a deformation of an order of 0.01 mm. In such a case, the result is a force level that substantially corresponds to standing on a rigid base.

Instead of force measurement detectors that measure the force directly, in an embodiment of the invention, it is possible to use any detectors whatsoever by whose means of it possible to measure loads applied from the measurement base to the rigid support base.

In practice, the measurement data given by the force detectors or equivalent are read at certain intervals and, when the readings are stabilized, average values are calculated in order that the measurement should be sufficiently reliable. The force measurement results of the inside of the foot obtained in this way are compared with the corresponding results of the outside, and the ratio obtained is used as the criterion of choice of the shoes and insoles. The device in accordance with the invention is provided with a microprocessor for the processing of the measurement results as well as for carrying out the selection, whereby the method of the invention has become as rapid and automatic as possible.

The examples provided above are not meant to be exclusive. Many other variations of the present invention would be obvious to those skilled in the art, and are contemplated to be within the scope of the appended claims.

I claim:

1. A method for selecting an insole and/or a show that adjusts the posture of a foot and/or for determination of the biomechanical mode of operation of the foot of a human subject, comprising
    placing a foot of the subject along a symmetry axis of a measurement base support on a rigid base,
    providing measurement means on said rigid base at equidistant, symmetrical locations on both sides of the symmetry axis,
    providing said measurement base with an articulated joint structured and arranged to pivot said measurement base about the symmetry axis in response to pronation or supination of a foot being placed on said measurement base,
    providing a pair of said measurement bases to constitute a right and left measurement base for the corresponding feet of the subject,
    measuring a load applied by the respective foot to said right and left measurement bases in relation to the symmetry axis of said right and left measurement bases, said load being measured on both sides of said symmetry axis of said right and left measurement bases via said measurement means; and
    carrying out said measurement of the load applied to said right and left measurement bases when the subject stands on both of said right and left measurement bases with the subject's legs in a straight posture position, each of said measurements being used to determine the extend of supination or pronation of the respective foot placed on said right and left measurement bases.

2. The method of claim 1, further comprising
    placing the heel of the foot in a centering guide fork arranged at an end of said measurement base and along the symmetry axis of the measurement base, and
    aligning a symmetry axis of the foot defined by an axis running through the root joint of the middle toe and a center point of said guide fork with said symmetry axis of said measurement base by guiding the position of the foot onto said symmetry axis by the heel and by the toes of the foot.

3. The method of claim 1, further comprising carrying out the measurement of the load in two stages so that first the load is measured when the subject stands on said right and left measurement bases with the subject's legs in a straight position, and thereafter measuring the loading when the knees of the subject are bent substantially 45° from the straight posture position.

4. The method of claim 3, further comprising keeping the distance between the knees of the subject substantially invariable during said second stage of the measurement of the load, when the knees are being bent.

5. The method of claim 1, wherein the load of the foot is measured by at least two and not more than four points on said rigid base.

6. The method of claim 1, further comprising arranging said right and left measurements bases at an angle of about 16° in relation to a forward direction in which the subject's body faces.

7. The method of claim 1, further comprising obtaining the ratio of a measurement obtained from one of said measurement detectors which measures the load on an outside edge of the foot on said measurement base and from a second one of said measurement detectors which measures the load on an inside edge of the foot on said measurement base and selecting a shoe to provide for the correct support of the foot based on said ratio.

8. The method of claim 1, further comprising arranging said measurement detectors such that the deformation in said detectors is sufficiently small to prevent a measurement error from being caused by a change in position of said measurement base.

9. The method of claim 1, further comprising choosing the insole or shoe for the right and left feet of the subject based on said measurements from said right and left measurement bases, respectively.

10. A device for determining the biomechanical mode of operation of the feet of the human subject and/or for the selection of an insole and/or of a shoe that adjusts the posture of the foot, comprising

- a measurement base structured and arranged such that a foot of the subject can be placed thereon,
- a guide fork located on a longitudinal symmetry axis of said measurement base for the heel of the foot of the subject, said longitudinal symmetry axis of said measurement base substantially corresponding to a symmetry axis of a human foot defined by an axis running through the root joint of the middle toe and a center point of said guide fork,
- a rigid base, said measurement base being supported on said rigid base,
- an articulated joint connected to said measurement base, said articulated joint being structured and arranged to pivot said measurement base about the longitudinal symmetry axis in response to pronation or supination of the foot being placed on said measurement base, and
- measurement detectors arrange dons aid rigid base for measuring loads applied by the foot to said measurement base, said load being measured in relation to the longitudinal symmetry axis of said measurement base and used to determine the extent of supination or pronation of the foot placed on said measurement base, said measurement detectors being arranged substantially symmetrically to the longitudinal symmetry axis of said measurement base.

11. The device of claim 10, wherein said measurement base is supported on said rigid base at three support points, said articulated joint being arranged at a front part of said measurement base and constituting a front support point, and two rear support points being arranged at a rear part of the measurement base, said rear support points being placed symmetrically in relation to the symmetry axis of said measurement base and being provided with measurement detectors.

12. The device of claim 10, wherein said guide fork is located at a rear part of the measurement base and arranged to align the symmetry axis of the foot with said symmetry axis of said measurement base.

13. The device of claim 10, comprising at least two and not more than four measurement detectors.

14. A device for determining the biomechanical mode of operation of the feet of a human subject and/or for the selection of an insole and/or of a shoe that adjusts the posture of the foot, comprising

- a right and left measurement base structured and arrange such that the right and left foot of the subject can be placed on said right and left measurement bases respectively and apply a load thereto,
- an articulated joint connected to each of said right and left measurement bases, said articulated joint being structured and arranged to pivot said measurement base about a longitudinal symmetry axis of said measurement base in response to pronation or supination of the foot being placed on said measurement base,
- a guide fork located on the longitudinal symmetry axis of each of said measurement bases for the heel of the corresponding foot of the subject, said longitudinal symmetry axis of said measurement base substantially corresponding to a symmetry axis of a human foot and defined by an axis running through the root joint of the middle toe and a center point of said guide fork,
- rigid bases, supporting each of said measurement bases, and
- measurement detectors arranged on said rigid bases for measuring loads applied by the foot to said measurement bases, said load being measured in relation to the longitudinal symmetry axis of each of said measurement bases and being used to determine the extent of supination or pronation of the foot placed on each of said measurement bases, said measurement detectors being arranged substantially symmetrically to the longitudinal symmetry axis of each of said measurement bases.

15. The device of claim 14, wherein said right and left measurements bases are arranged at an angle of about 16° in relation to a forward direction in which the subject's body faces.

* * * * *